United States Patent [19]
Kowatsch et al.

[11] Patent Number: 5,580,530
[45] Date of Patent: Dec. 3, 1996

[54] DEVICE FOR VAPOR STERILIZATION OF ARTICLES HAVING LUMENS

[75] Inventors: Reinhard Kowatsch, Hamburg, Germany; Toby Soto, Fort Worth, Tex.; Charles Howlett, Laguna Beach, Calif.

[73] Assignee: Johnson & Johnson Medical, Inc., Arlington, Tex.

[21] Appl. No.: 436,999

[22] Filed: May 8, 1995

Related U.S. Application Data

[63] Continuation-in-part of Ser. No. 120,303, Sep. 13, 1993, which is a continuation of Ser. No. 864,151, Apr. 2, 1992, abandoned, which is a continuation of Ser. No. 464,843, Jan. 16, 1990, abandoned, which is a division of Ser. No. 79,550, Jul. 30, 1987, Pat. No. 4,943,414.

[51] Int. Cl.$^6$ ..................... A61L 2/20
[52] U.S. Cl. ............... 422/102; 422/103; 422/292; 422/305; 220/278
[58] Field of Search .............. 422/102, 292, 422/294, 302, 303, 103, 305; 220/278; 604/411, 415

[56] References Cited

U.S. PATENT DOCUMENTS

| | | |
|---|---|---|
| 1,817,530 | 8/1931 | Spanel . |
| 2,688,428 | 9/1954 | Manhartsberger ............... 220/278 X |
| 3,371,985 | 3/1968 | Wyka . |
| 3,688,985 | 9/1972 | Engel . |
| 3,730,434 | 5/1973 | Engel . |
| 4,152,378 | 5/1979 | Vcelka et al. .................. 220/278 X |
| 4,169,123 | 9/1979 | Moore et al. . |
| 4,380,530 | 4/1983 | Kaye . |
| 4,410,492 | 10/1983 | Kaye . |
| 4,525,220 | 6/1985 | Sasa et al. . |
| 4,526,622 | 7/1985 | Takamura et al. . |
| 4,526,623 | 7/1985 | Ishii et al. . |
| 4,576,650 | 3/1986 | Yabe et al. . |
| 4,579,597 | 4/1986 | Sasa et al. . |
| 4,579,598 | 4/1986 | Sasa et al. . |
| 4,643,876 | 2/1987 | Jacobs et al. . |
| 4,675,159 | 6/1987 | Al-Sioufi . |
| 4,756,882 | 7/1988 | Jacobs et al. . |
| 4,808,381 | 2/1989 | McGregor et al. . |
| 4,867,326 | 9/1989 | O'Meara ........................ 220/278 X |
| 4,943,414 | 7/1990 | Jacobs et al. ..................... 422/28 |
| 4,956,145 | 9/1990 | Cummings et al. . |
| 5,084,239 | 1/1992 | Moulton et al. . |
| 5,171,214 | 12/1992 | Kolber et al. .................. 604/411 X |
| 5,186,893 | 2/1993 | Moulton et al. . |
| 5,244,629 | 9/1993 | Caputo et al. . |
| 5,260,021 | 11/1993 | Zeleznick . |
| 5,288,460 | 2/1994 | Caputo et al. . |
| 5,310,524 | 5/1994 | Campbell et al. . |
| 5,362,444 | 11/1994 | Amtower . |
| 5,364,386 | 11/1994 | Fukuoka et al. ..................... 604/411 |

OTHER PUBLICATIONS

Fisher Scientific Catalogue, pp. 46c–47c (1983).
Product Label for Sterrad* Adapter (1993).
Directions for Use Sterrad* Adapter (1994).

*Primary Examiner*—Jeffrey Snay
*Attorney, Agent, or Firm*—Andy C. Farmer

[57] ABSTRACT

A method and device for enhancing the vapor sterilization of the lumen of medical instruments and like articles under reduced pressure. A vessel containing a small amount of a vaporizable liquid antimicrobial solution is attached to the lumen. The antimicrobial vaporizes and flows directly into the lumen of the article as the pressure is reduced for the sterilization cycle. Preferred embodiments illustrate a sealed chamber containing the antimicrobial and an opener for opening the chamber with the device already attached to the article. Preferably, the opener comprises a hollow spike. A ring between the opener and chamber must be removed prior to opening the chamber and removal of the ring destroys the ring so that it can not be replaced.

23 Claims, 11 Drawing Sheets

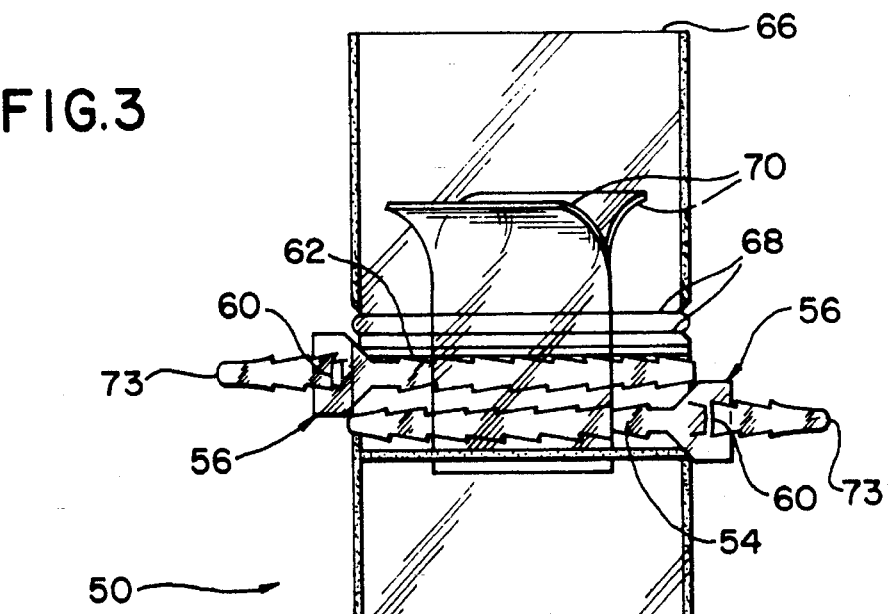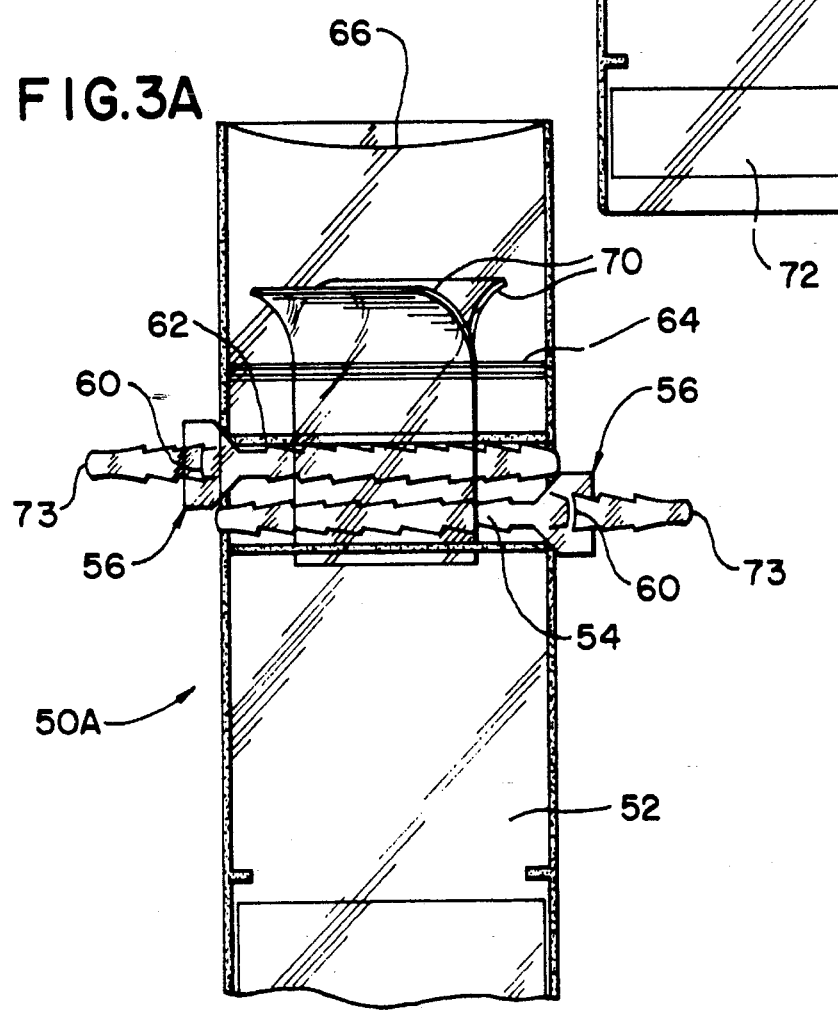

DEVICE FOR VAPOR STERILIZATION OF ARTICLES HAVING LUMENS

This is a continuation-in-part of application Ser. No. 08/120,303 filed Sep. 13, 1993, which is a continuation of application Ser. No. 07/864,151 filed Apr. 2, 1992, now abandoned, which is a continuation of application Ser. No. 07/464,843 filed Jan. 16, 1990, now abandoned, which is a division of application Ser. No. 07/079,550 filed Jul. 30, 1987, now U.S. Pat. No. 4,943,414, issued Jul. 24, 1990.

BACKGROUND OF INVENTION

1. Field of Invention

The invention relates to the vapor sterilization of articles such as medical instruments having long narrow lumens therein, and more particularly, to a device for delivering a gaseous antimicrobial directly into the lumen of an article during the sterilization process.

2. Background Information

The need to sterilize articles such as medical instruments and others for use in the agriculture and fermentation industries is well known. In recent years, many methods of vapor sterilization have been developed. While these methods offer the advantage of being generally faster than sterilization by immersion in an antimicrobial solution, they suffer from one major disadvantage, namely the inability to sterilize the interior of a long narrow tube in a short period of time. Thus, with regard to medical instruments such as endoscopes, the difficulty in sterilizing the lumen can often negate the general advantage of using vapor sterilization.

One way of overcoming the above disadvantage is set forth in U.S. Pat. Nos. 4,410,492 and 4,337,223. The apparatus described therein comprises a sterilizing chamber with means for introducing an antimicrobial gas into the chamber and circulating the gas within the chamber. Disposed within the chamber is a socket for receiving the tubular end of a medical instrument. The socket is connected to a valve and a recirculating pump and the antimicrobial gas is recirculated from the chamber through the lumen of the instrument. The commercial apparatus employs ethylene oxide as the antimicrobial and requires a sterilization times of about 3 hours for flexible endoscopes and about 2 hours for the shorter, rigid endoscopes. Ethylene oxide is a known toxic substance and the process thereby experiences concomitant toxicity problems. In addition, the method and apparatus described in these references cannot be used to sterilize an instrument within a sterile pack since one end of the instrument must be attached to the socket.

Thus there is a current need for an effective method to sterilize medical instruments such as endoscopes in a reasonably short period of time, preferably in one hour or less. The method and device of the present invention makes vapor sterilization of such instruments practical by delivering vapor directly to the interior of the lumen in the endoscope, whether or not it is in a sterile pack.

SUMMARY OF THE INVENTION

The present invention comprises a method and device for providing antimicrobial vapor directly into the long narrow lumen of medical instruments and similar articles. The device and method are intended for use with solution vapor sterilization procedures. In these procedures, the article is placed within a sterilization chamber, the pressure in the chamber is reduced, and a liquid solution of antimicrobial agent is introduced into the chamber where it vaporizes. Alternatively, an antimicrobial vapor may be introduced directly into the chamber after the pressure therein has been reduced. In either case, the instrument is sterilized by exposure to the vapor or active species generated from it rather than by direct contact with a liquid antimicrobial. The procedure may further involve the use of heat or, e.g., low pressure gas plasma to enhance the antimicrobial activity, reduce sterilization times, and/or remove residual any antimicrobial agent from the instrument.

In its simplest form, the device of the present invention comprises a vessel containing a small amount of the antimicrobial solution, and a means for connecting the vessel to the lumen of the instrument to provide a source of antimicrobial vapor directly to the lumen during the vapor sterilization process. The device is placed on the instrument prior to disposing the instrument in the sterilization chamber. As the pressure in the chamber is reduced, the antimicrobial solution contained in the vessel is vaporized and passes from the vessel into the lumen of the instrument.

With the use of the device and method of the present invention, vapor sterilization times for endoscopes can be reduced to one hour or less. In addition, the method and the device may be used to sterilize endoscopes in a sterile pack since the device of the present invention may be attached to and packaged with the endoscope before the endoscope is placed within the sterilization chamber. Upon opening of the pack, the device may be retrieved for re-use or preferably discarded with the pack.

The device and method of the present invention reduce sterilization time required for instruments having long narrow lumens therein. Reduced sterilization times are also achieved with the instruments encased in a package designed to maintain sterility after the removal from the sterilized chamber. In addition, as antimicrobial vapor is provided directly into the lumen of the instrument, lower concentrations of antimicrobial solutions may be used in the sterilizer, and this together with the reduced sterilization times provides improved materials compatibility with respect to both the instrument components and the packaging or wrapping materials.

A device according to the inventions delivers an antimicrobial vapor to a lumen of an article during solution vapor sterilization. The device comprises a first member which comprises a vessel having an inner sealed chamber containing an antimicrobial solution and a wall forming at least a portion of the chamber. A connector connects the vessel to the article lumen. A second member connects to the first member in moveable relation thereto. The second member comprises an opening member whereby movement of the second member in a predetermined direction relative to the first member moves the opening member toward wall to open the wall and place the chamber into fluid communication with the article lumen.

Preferably, the opening member opens the wall via penetration thereof and comprises a spike having a first end and a second end, and wherein the first end faces the wall and comprises a sharpened tip. Preferably, a central lumen extends coaxially through the spike and communicates with the connector whereby the vessel is placed into fluid communication with the article lumen through the spike lumen when the spike penetrates the wall.

Preferably, the first and second members interconnect in telescoping relationship with each other. A detent and surface on the opposing members preferably limits the degree to which the first and second members can telescope apart.

To ease the breaching of the wall a threaded interconnection can be provided between the first and second members wherein rotation of the first and second members relative to each other moves them together to breach the wall. A tactile detent can be provided to let a user know when the members are fully rotated together.

Preferably, a guard is disposed between abutting surfaces on the first and second members to prevent the first and second members from moving together sufficiently to breach the wall. The guard preferably has a contrasting appearance to the first and second members whereby the presence or absence of the guard can easily be visually determined. In a preferred form, the guard comprises a ring encircling the device between the first and second members and is inelastic so that to remove the ring from between the first and second abutting surfaces it must be deformed beyond its elastic limit.

BRIEF DESCRIPTION OF THE DRAWINGS

FIG. 3 is a plan view of another embodiment of a device of the present invention;

FIG. 3A is a variation of the device of FIG. 3;

DETAILED DESCRIPTION OF THE INVENTION

Figure 1:
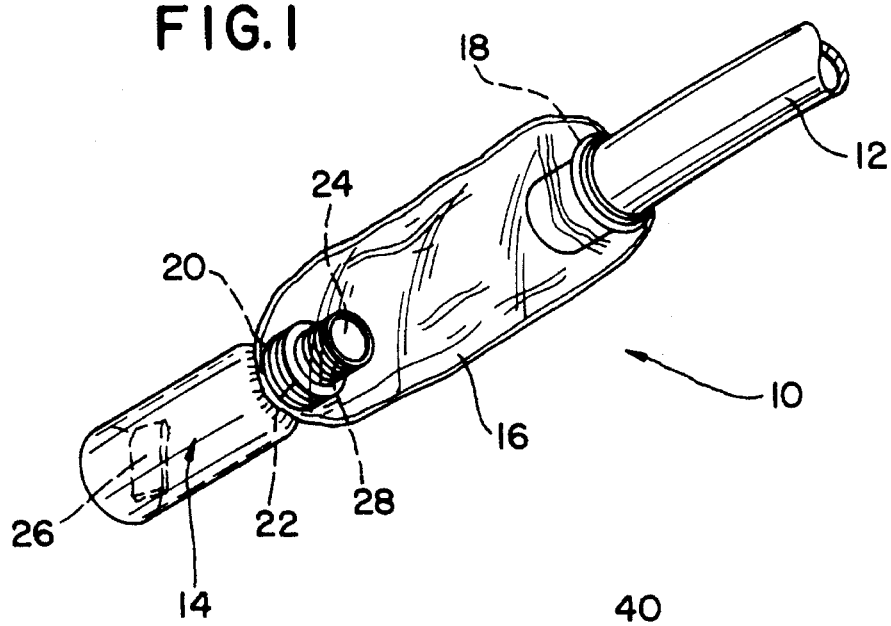
FIG. 1 is a perspective view of one embodiment of the device, according to the present invention, attached to the end of a tube.

The method and device of the present invention relates to the sterilization of articles such as medical instruments having a long narrow tube therein. The term instruments as used herein applies to medical or surgical devices such as endoscopes, catheters, tubing, or similar instruments or articles having am internal lumen which is preferably used in a sterile condition as in, for example, the agricultural or fermentation industries. The method and device of the present application show particular advantages in the solution vapor sterilization of lumens exceeding ten centimeters in length and having an internal diameter of about 7 millimeters or less. As endoscopes typically have lumens with internal diameters of 1 to 4 millimeters and lengths of up to 1.5 meters or more for flexible endoscopes and at least 45 centimeters for rigid endoscopes, the method and device of the present application have particular applicability to the sterilization of these instruments. With the use of the device of the present invention, antimicrobial vapor is supplied directly to the lumen or interior of the tube of the instrument during the vapor sterilization process.

The antimicrobials used with the method and device of the present invention include solutions of glutaraldehyde, hydrogen peroxide, chlorine dioxide or other antimicrobials in an inert solvent, the only requirement being that the solution be liquid at atmospheric pressure and a vapor at the temperature and pressure of the sterilization process. Though the higher concentration solutions of antimicrobials are more effective, problems with materials compatibility and shipping and handling may arise at very high concentrations. For example, a 30% to 50% solution of hydrogen peroxide in water is both very effective and presents few shipping and handling problems, while higher concentrations of up to 70% become increasingly more difficult and dangerous to handle.

In solution vapor sterilization, the procedure generally used is as follows: The article to be sterilized is placed within the sterilization chamber, the chamber is sealed, and a vacuum is drawn on the chamber to reduce the pressure to less than about 50 torr, and preferably to 20 torr or less. An antimicrobial solution is then injected into the chamber where it vaporizes and contacts the exposed surfaces of article. The time necessary for total kill of specific microbial agents varies with the type and concentration of antimicrobials present, and with the degree of exposure to the microbial agent. Microbials disposed in cracks, crevices or internal tubular structures are somewhat protected from the antimicrobial agent and require more time for total kill than microbials on the external surface of the article. Heat or high frequency radiation may be used to increase the effectiveness of the antimicrobial and its penetration into remote areas of the instrument.

The device of the present invention comprises a vessel for containing a small amount of antimicrobial solution, and a means for connecting the vessel directly to the lumen or the end of the tube of the article to be sterilized. When the article with device containing antimicrobial solution is disposed in the sterilization chamber and a vacuum drawn on the chamber, antimicrobial vapor generated from the solution within the vessel flows directly into the lumen.

The effectiveness of the method and device of the present invention was demonstrated by the following experiments:

50 inch (127 centimeters) lengths of Tygon tubing having a 2 millimeter inside diameter were used to simulate an endoscope in the sterilization test. A paper strip (2 mm×13 mm) containing approximately $2.0 \times 10^6$ Bacillus subtilis (var. globigii) spores was placed in each tube equidistant from each end. A syringe containing 0.05 milliliters of 10% by weight hydrogen peroxide solution in water was provided for each tube. Each of the samples was individually packaged in a TYVEK™/MYLAR™ envelope prior to sterilization.

One third of the samples (three units) were placed in the package with the syringe unattached to the end of the tube. Another one-third of the samples were packaged with the syringe attached. Individual samples were placed within a 65 liter sterilization chamber and sent through a hydrogen peroxide vapor sterilization cycle wherein the pressure within the chamber was reduced to 3 torr for the total exposure time minus 15 minutes, and 0.5 torr for the final 15 minutes of exposure. No additional hydrogen peroxide was injected into the chamber.

The remaining one-third of the samples, packaged with the syringe attached to the end of the tube as described above, were sent through a hydrogen peroxide vapor sterilization cycle supplemented with high frequency radiation plasma which is known to generate an active species from the hydrogen peroxide. Again a 65 liter chamber was used, and the pressure within the chamber was reduced to 3.0 torr for the total exposure time minus 15 minutes and 0.5 torr for the final 15 minutes of exposure. Again, no additional hydrogen peroxide was injected into the chamber. Plasma was generated only during the final 15 minutes of exposure at 2.05 MHz with 320 watts of power, pulsed 0.3 milliseconds on to 1.0 milliseconds off.

At the conclusion of the sterilization cycle, the paper strip was removed from each tube and placed in a glass vial containing 10 ml of a sterile pH 7.0 phosphate buffer solution. This solution contained 10 milligrams of TWEEN 80 to aid in removal of any spores from the paper strip and 0.0066 milligram of catalase to neutralize any remaining hydrogen peroxide. Five glass beads were placed in the solution, and the solution was vortexed for two minutes to completely macerate the paper strip. Three decimal dilutions of the solution were made with sterile pH 7.0 phosphate buffer, and the original solution and the decimal dilutions were poured into sterile glass Petri plates. A culture medium was added and the plates were incubated for four days at 30° C. After incubation the number of viable organisms in each plate was counted, and the number of spores on the paper strip calculated by multiplying the spore count by the appropriate dilution factor.

Figure 4:
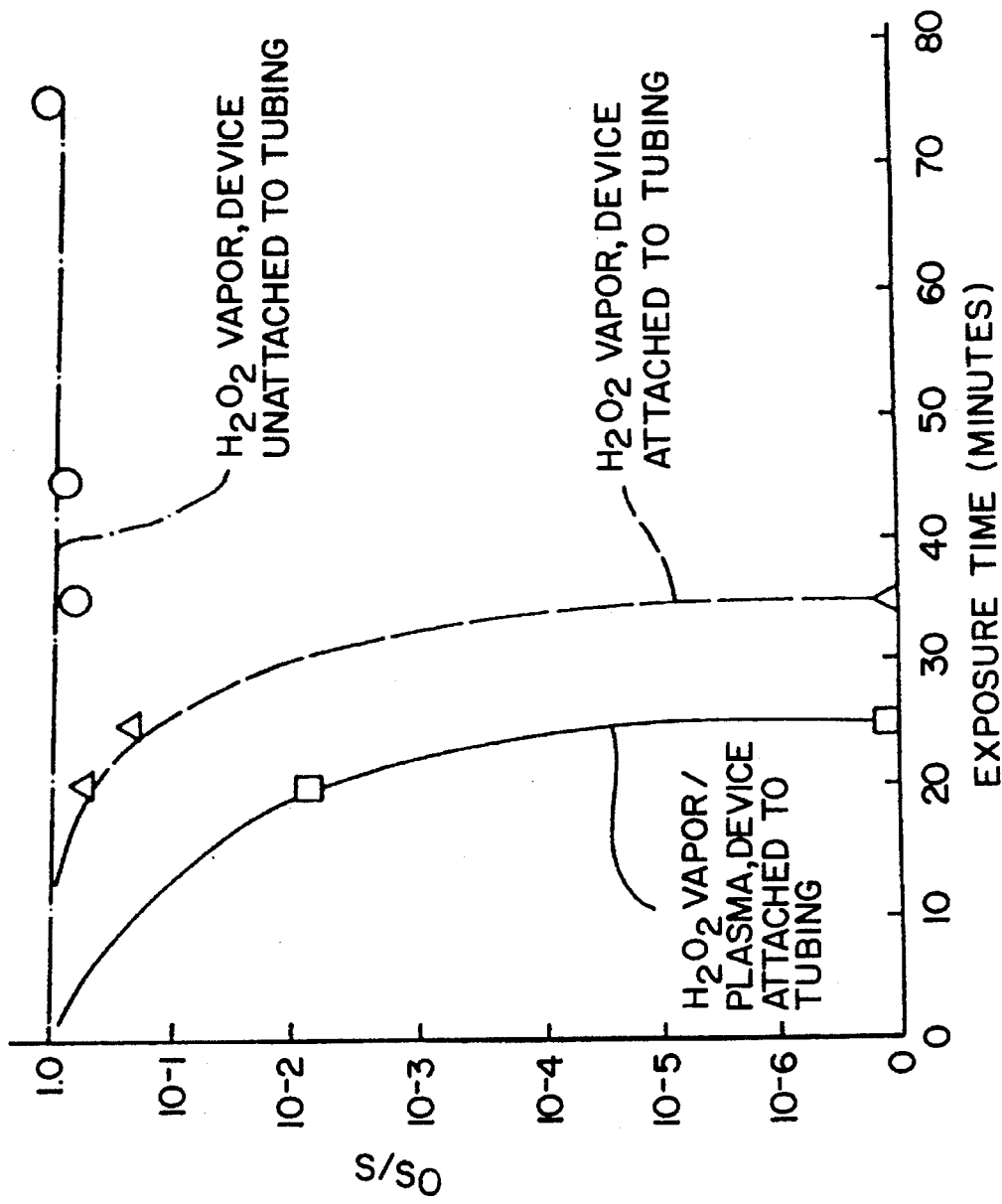
FIG. 4 is a plot of sterilization time verses efficacy and showing enhanced efficacy of attaching an $H_2O_2$ device to a lumen prior to sterilization.

The results of the experiments are presented in Table I below, and plotted in FIG. 4, where $S/S_0$ represents the ratio of the number of organisms surviving the test to the initial number of organisms which were placed on the paper strip prior to the test. As shown by these data, no reduction in microbial population was achieved in samples where the syringe was not attached to the tubing, even after an exposure time of 75 minutes. Attaching the syringe to the end of the tube according to the method of the present invention produced total kill in 35 minutes without low temperature gas plasma, and in 25 minutes when the antimicrobial activity was enhanced by the use of low temperature gas plasma.

TABLE I

| Sample | Sterilization Time - Min. | Efficacy ($S/S_0$) |
|---|---|---|
| A | 35 | $8.6 \times 10^{-1}$ |
|   | 45 | $8.9 \times 10^{-1}$ |
|   | 75 | $1.1 \times 10^{-0}$ |
| B | 20 | $7.0 \times 10^{-1}$ |
|   | 25 | $5.8 \times 10^{-1}$ |
|   | 35 | 0 |
| C | 20 | $8.5 \times 10^{-3}$ |
|   | 25 | 0 |
|   | 35 | 0 |

Sample A - Syringe unattached
Sample B - Syringe attached
Sample C - Syringe attached plus plasma A preferred embodiment of the device to be used in accordance with the teaching of the present invention is shown in FIG. 1. The device indicated generally at 10 is shown attached to a tube 12. In the device depicted in FIG. 1. the means for connecting the vessel 14 to the end of the tube comprises an expandable sheath 16, one end of which is securely attached to the vessel, and the other end of which comprises an elastic ring 18 making a releasable attachment about the end of the tube. The sheath 16 may be attached to the vessel in any known manner and, as shown in FIG. 1, the sheath 16 is attached to the vessel by a second elastic ring 20 disposed over the lip 22 about opening 24 of vessel 14. Though the vessel shown is cylindrical, the vessel may comprise any three dimensional container preferably of semi-rigid material, having an opening therein. The vessel may be made of, e.g., polyethylene, polypropylene, glass or any other material which is nonreactive to the antimicrobial solution of vapor. The sheath may also be formed of polyethylene, polypropylene or other material which is relatively nonreactive to the antimicrobial vapor. The elastic rings may be formed of natural latex or butyl rubber which are relatively resistant to the antimicrobial vapors; however, resistivity is less critical when the device is constructed for one time use. Disposed within the vessel may be a substrate 26 comprising a woven or nonwoven fabric or sponge for containing the liquid antimicrobial solution. The vessel preferably has a means 28 associated with the opening for attaching a closure cap over the opening prior to use in order to maintain the antimicrobial solution therein. As shown in FIG. 1, means 28 comprises threads for a screw cap fitting about the lip of the vessel.

Figure 2:
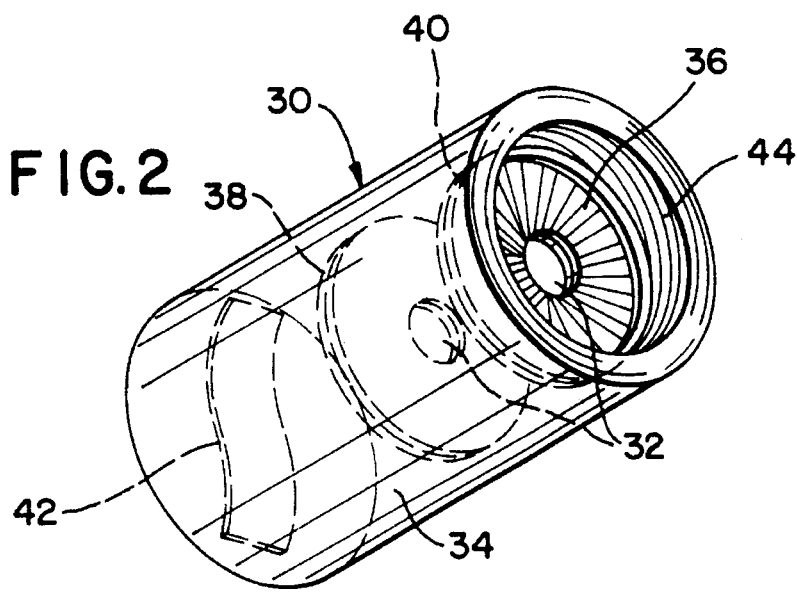
FIG. 2 is a perspective view of another embodiment of the device of the present invention, showing the end of the device for making a connection to a tubular member.

Another embodiment of the device of the present invention is depicted in FIG. 2 where the device is indicated generally at 30. The means for connecting the vessel 34 to the end of a tubular instrument comprises a bushing 36 disposed within the open end of the vessel. In the particular embodiment shown in FIG. 2, the bushing comprises a series of rings 38 and 40 of inwardly extending plastic flaps defining a flexible aperture 32 to receive the tubular instrument. The flaps can be made of any flexible material which is non-reactive to the antimicrobial solution or vapor, such as polyethylene, and of sufficient thickness that the flaps provide resistance to withdrawal of a tube inserted through the aperture. Disposed within the vessel is a substrate 42 containing the antimicrobial solution. Preferably, the vessel 34 is provided with means 44 for attaching a closure cap thereto prior to use. As shown in FIG. 2, means 44 comprise threads for attaching a screw cap (not shown) within the opening of the vessel.

Figure 2A:
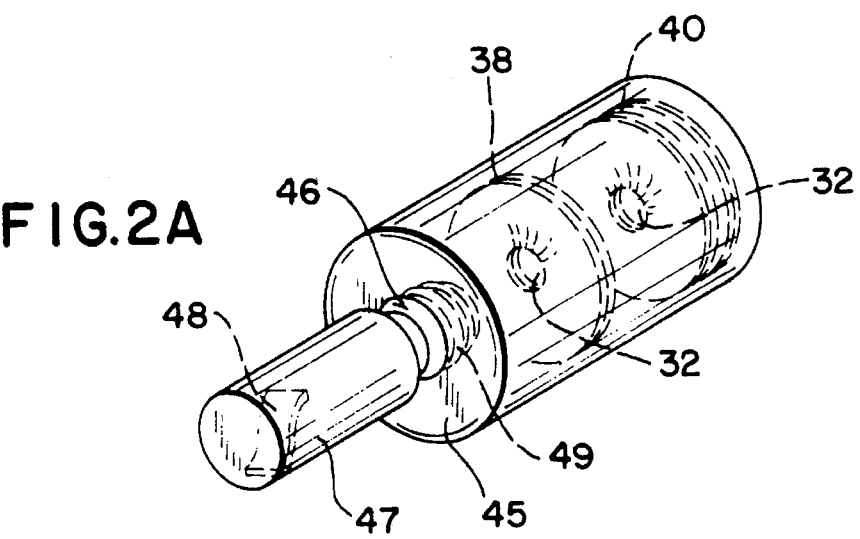
FIG. 2A is a perspective view of a variation of the device of FIG. 2.

FIG. 2A illustrates a variation in the design of the device of FIG. 2 which utilizes the same basic vessel and means for attachment to a tubular device. In the device shown in FIG. 2A, end 45 of the vessel opposite the open end is provided with aperture 46 for attaching a disposable cartridge 47 containing a supply of antimicrobial on a substrate such as a woven or nonwoven fabric or sponge 48 as illustrated. The aperture 46 of the vessel is designed in conjunction with neck 49 of the cartridge to provide quick and easy attachment and release of the cartridge and the vessel. In the embodiment shown in FIG. 2A, aperture 46 is provided with reverse threads for engaging the threads of the neck 49 of the cartridge. In this variation of the device it is not necessary for a substrate containing the antimicrobial solution to be disposed within the vessel since the antimicrobial solution is provided in pre-measured aliquots in the cartridges. With the device of FIG. 2A one achieves the convenience and accuracy of disposable, pre-measured aliquots of antimicrobial solution without the expense associated with the device of FIG. 2.

The following table sets forth the effectiveness of the devices depicted in FIGS. 1 and 2 in a sterilization procedure described below.

TABLE II

Effect of Devices on Efficacy of Sterilization Inside Tubes

| Material | I. D. (cm) | Length (cm) | Efficacy ($S/S_0$) | | |
|---|---|---|---|---|---|
| | | | No Device | FIG. 1 | FIG. 2A |
| Surgical Tygon | 0.64 | 10 | 0 | — | — |
| | 0.64 | 20 | $4.4 \times 10^{-5}$ | — | — |
| | 0.64 | 30 | $1.1 \times 10^{-2}$ | — | — |
| | 0.64 | 45 | $8.8 \times 10^{-1}$ | 0 | 0 |
| Rubber Tubing | 0.64 | 25 | $1.7 \times 10^{-1}$ | — | — |
| | 0.64 | 45 | $7.9 \times 10^{-1}$ | 0 | 0 |

The efficacy is recorded in terms of the ratio of the number of microorganisms surviving the test, S, to the number of challenge organisms, $S_0$ (approx. $1 \times 10_6$) on a paper strip disposed within the tube equidistant from the ends. In the sterilization procedure, 100 microliters of 30% aqueous $H_2O_2$ solution was supplied in each of the devices. The devices were attached to the ends of tubes of the indicated length and 0.64 cm in internal diameter. All of the tube samples were placed within TYVEK'/MYLAR' packaging prior to sterilization, The packaged tubes were placed within the sterilizing chamber and the pressure therein was reduced to about 0.1 torr in about 10 minutes. Additional 30% $H_2O_2$ solution was injected into the chamber to achieve a concentration of 2.0 milligrams $H_2O_2$ per liter of chamber volume. Following injection of the $H_2O_2$, the tubes were retained in the chamber an additional 50 minutes.

Injection of the $H_2O_2$ solution raised the pressure in the chamber to about 6 torr and the pressure was again reduced to about 0.1 torr. During the last 10 minutes of exposure, low temperature gas plasma was generated in the chamber at 300 watts. The challenge micro organisms used in the test were *Bacillus subtilis* (var. globigii) spores.

As shown in Table II above, when the tube length was only 10 centimeters, sterilization was achieved without the use of the device according to the present invention. However, for tubing of 20 and 30 centimeters in length, a device of the present invention would be needed in order to achieve sterility within the exposure time of the test. For tubes of 45 centimeters in length, total kill was achieved during the 1 hour exposure time of the test, using either of the devices depicted in FIG. 1 and FIG. 2.

A further experiment used 7 mm medical grade Teflon tubing 183 cm in length. The tubing was cut into three pieces to obtain a 5 cm long center section which was joined in the end sections by external tubing connectors. In the experiment, approximately $1.0 \times 10_4$ Bacillus (var. globigii) spores were deposited in the center section of the Teflon tubing. The tubing was assembled and subjected to sterilization with hydrogen peroxide vapor as described above at a concentration of 2.0 mg./liter of chamber volume. The chamber was evacuated to a pressure of 0.1 torr before the peroxide was injected as an aqueous solution and allowed to vaporize. After 20 minutes, a continuous gas plasma was generated in the chamber at 300 watts, 13.5 MegaHertz and the sterilization continued for an additional 5 minutes after which the vacuum was released with sterile, filtered air, and the number of surviving spores determined.

The experiment was first conducted without a device of the present invention attached to the tubing, then repeated with a device of FIG. 3 as described below containing 100 ml of 30% hydrogen peroxide attached to one end of the tubing. The experimental results of the tests are presented in Table III below.

TABLE III

Sterilization of 1 mm Tubing Efficacy ($S/S_0$)

| Material | I.D. | Length | No Device | FIG. 1 Device |
|---|---|---|---|---|
| Teflon | 1 mm | 183 cm | $1.9 \times 10^{-1}$ | 0 |

The data of Table III demonstrate the efficacy of the method of the present invention in sterilizing of very long tubes having very small diameters used in certain endoscopic procedures.

Additional embodiments of the device of the present invention are depicted in FIGS. 3 and 3A. The device shown in FIG. 3 indicated generally at 50, comprises a vessel 52 in the form of a pouch constructed of a flexible material. The means for connecting the vessel or pouch 52 to the end of an instrument tube comprises a first drawstring 54, and preferably a second drawstring 62. These drawstrings are preferably arranged in the configuration as shown in FIG. 2 to be drawn from opposite sides of the pouch. The pouch is preferably provided with an airtight seal to maintain the antimicrobial solution therein prior to use, and includes a means for creating an opening in the sealed pouch so that it may be disposed over the end of a tube. The seal may be created by sealing the ends 66 of the pouch, and of the lumen as often the means for opening the sealed pouch may comprise, for example, a line of weakening at 68, preferably in combination with a notch also shown generally at 68, to permit the pouch to be opened by tearing off one end.

FIG. 3A shows a device indicated generally at 50A, similar to device 50, but wherein the airtight seal and the means for creating and opening the sealed pouch is a line of fastening 64 similar to a "zip-lock" closure. Optionally, opening flaps 70 may be provided on either side of the pouch adjacent closure 64 of FIG. 3A, or the line of weakening 68 of FIG. 3. These flaps are firmly secured to the pouch. In use, after the sealed end 66 of the pouch of FIG. 3 has been removed along the line of weakening 68, the flaps when pulled oppositely from each other will distend the opening of the pouch for disposal around the end of an instrument tube. The flaps of FIG. 3A, when pulled in opposite directions, can be used to open the zip-lock fastening, or if the fastening is already opened, to distend the opening for disposal around the end of an instrument tube. A substrate 72 such as a woven or nonwoven fabric or sponge may be disposed within the pouch for containing the antimicrobial solution.

In a preferred construction, the drawstrings are provided with a locking means as illustrated. Though many means for locking or catching a drawstring are known in the art and may be used in conjunction with the present invention, the locking means depicted at 56 at FIG. 3 comprise a catch 60 for a serrated edge 58 provided on the drawstring. As shown in FIG. 3, the catch, comprising an opening for disposing one end of the drawstring therethrough, is located at the opposite end of the drawstring. The catch, however, may be provided by a flap, opening therein, attached to the edge of the pouch, provided the other end of the drawstring must also be attached to the pouch. When two drawstrings are used, one or both drawstrings may be provided with a locking means. By pulling the end 73 of the drawstring, the flexible pouch is gathered and a firm fastening may be made to a tube inserted within the pouch.

Preferably, a highly concentrated solution of hydrogen peroxide is used as the liquid antimicrobial in the device of the present invention. However, in high concentrations, hydrogen peroxide can quickly cause damage to living tissue. A system for applying such solution to an instrument lumen while reducing the chances of accidental exposure of a user to the antimicrobial solution is highly desirable. The following embodiments provide such advantage.

Figure 5:
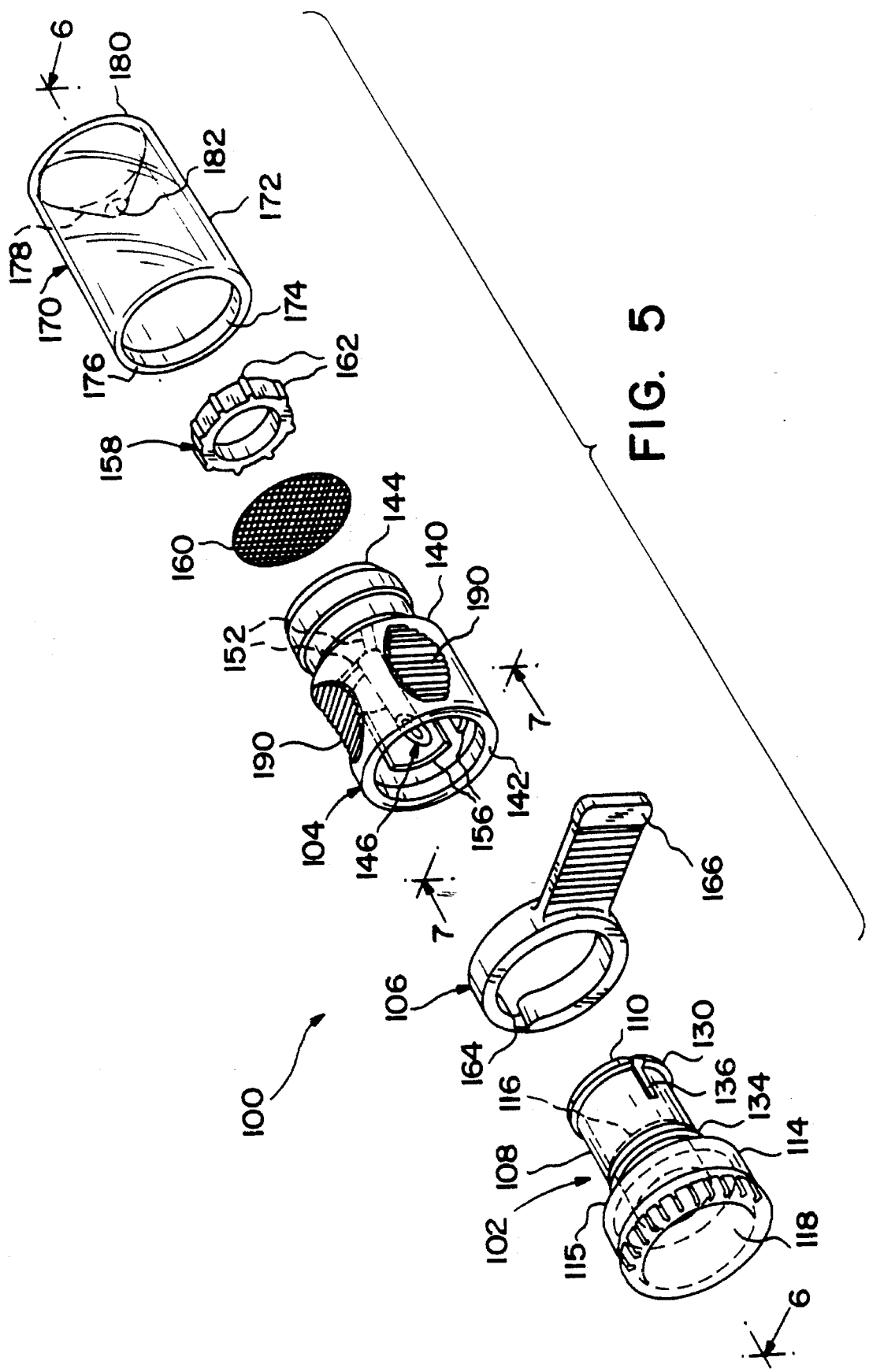
FIG. 5 is an exploded view of a further embodiment of a device of the present invention.
Figure 6:
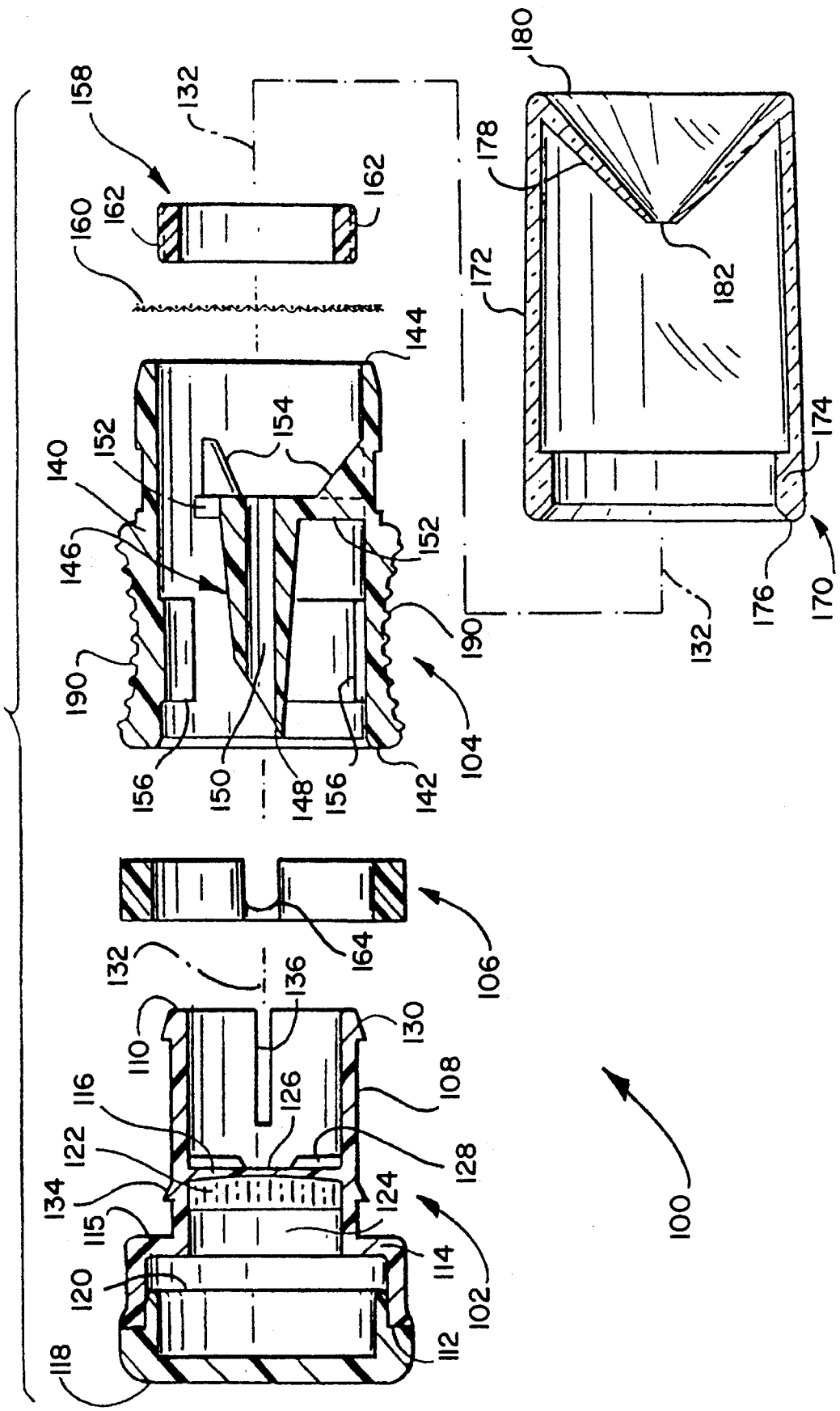
FIG. 6 is an exploded view in section of the device of FIG. 5.

FIG. 5 illustrates a further embodiment of a device 100 according to the invention. The device 100 comprises in gross a capsule 102, an opener 104, and a safety ring 106 positioned between the capsule of 102 and the opener 104. Turning to FIG. 6, the capsule 102 comprises a cylindrical body 108 having a distal end 110 and a proximal end 112. At the proximal end 112, the capsule body 108 expands radially to form a cup shaped well 114. A membrane wall 116 is disposed within the capsule body 108 adjacent to well 114.

A cap 118 of generally discoidal shape has a distally projecting annular flange 120 which fits within the well 114. The cap 118 is sonically welded to the capsule 102 at the proximal end 112 to seal a quantity of antimicrobial solution 122 within a chamber 124 defined between the cap 118, membrane wall 116 and capsule body 108. During storage the antimicrobial solution 122 may tend to diffuse through the capsule 102 and out of the chamber 124 thereby decreasing its quantity and potency. The antimicrobial solution 122 thus preferably comprises 197 mg of 59% hydrogen peroxide solution upon construction such that after a reasonable storage period such as ten months, the chamber 124 will retain approximately 100 mg of a 45% hydrogen peroxide solution.

So that it may be more easily breached, a central portion 126 of the membrane wall 116 has a slightly thinner thickness than the remainder of the membrane wall 116. Six radial ribs 128 extend from the capsule body 108 towards, but not into, the membrane wall central portion 126 to support the membrane wall 116 during the breaching process.

At the capsule body distal end 110, an annular flange 130 slopes outwardly and proximally, thus providing a barbed appearance in cross-section. The distal flange 130 preferably slopes in a gentle fashion, such as a 17° slope from an imaginary coaxial centerline 132 of the device 100. A central annular flange 134 slopes outwardly and proximally from the capsule body 108 at a slightly more aggressive angle than the distal flange 130. A pair of diametrically opposed slits 136 extend proximally in the capsule body 108 from its distal end 110 to allow some flexibility in the capsule body 108 and to thereby ease its entry into the opener 104.

The opener 104 comprises a cylindrical body 140 having a proximal end 142 facing the capsule 102 and a distal end 144. A hollow spike 146, coaxially disposed within the opener body 146, extends toward the membrane wall 116 and terminates in a beveled and sharpened tip 148. Preferably, the tip 148 is beveled at a 30° angle from the device center line 132. Also, a central lumen 150 extends coaxially through the spike 146.

Figure 7:
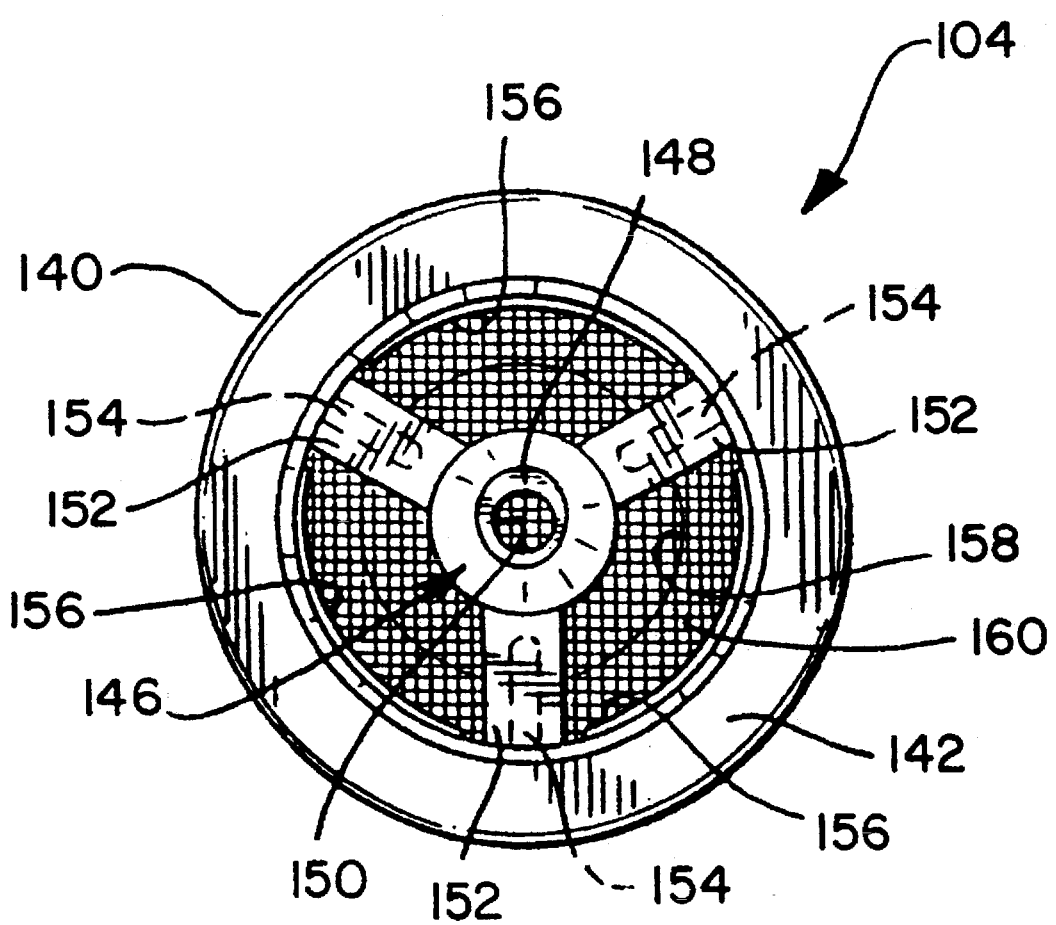
FIG. 7 is an end view of the opener of the device of FIG. 5.

Three equilaterally spaced posts 152 extend outwardly radially from a fixed end of the spike 146 to the opener body 140 and thereby support the spike 146 therein. Preferably, each of the posts 152 has a distally facing fillet brace 154 for added support. A circumferentially interrupted annular embossment 156 extends radially inwardly in a very shallow manner from the opener body 140 (see also FIG. 7). When the capsule 102 is inserted into the opener 104 with the capsule distal flange 130 beyond the opener embossment 156, engagement therebetween prevents the capsule 102 from being easily removed from the opener 104 while still allowing a relative degree of movement between the opener 104 and capsule 102 as will be more fully described hereinafter.

A retaining ring 158 holds a mist-filter screen 160 within the opener body distal end 144. The mist-filter screen 160 is round with a diameter exceeding that of the opener body 140 whereby it is frictionally retained within the opener body 140 by the retaining ring 158. Preferably, the mist-filter screen 160 has a mesh opening of 105 microns and is formed of polypropylene. A plurality of axially aligned embossments 162 on an outer surface of the retaining ring 158 ease insertion and securely retain the mist-filter screen 160 and retaining ring 158 within the opener body 140 (see also FIGS. 8 and 9).

Alternatively, a series of detents (not shown), each with a distally facing camming surface and a proximally facing radial surface could be provided within the opener body 140, axially adjacent the posts 152. The mist-filter screen 160 would thus have a diameter equal to the inside diameter of the opener body 140 and be held between the posts 152 and the proximally facing surfaces of the detents. The screen could be easily inserted through the opener distal end 144 and cammed over the detent camming surfaces into place between the posts 152 and detents.

The safety ring 106 separates the opener 104 from the capsule 102. With the safety ring 106 trapped between the opener body proximal end 142 and the lip 115 on the capsule 102, the spike 146 is prevented from contacting the membrane wall 116 (see also FIG. 8). The safety ring 106 is provided with a thin wall section 164 and a diametrically opposed pull tab 166 whereby manual pressure applied to the pull tab 166 is sufficient to deform the thin wall section 164 beyond its elastic limit, preferably breaching the thin wall section 164, thereby permitting removal of the safety ring 106 from the device 100.

Figure 8:
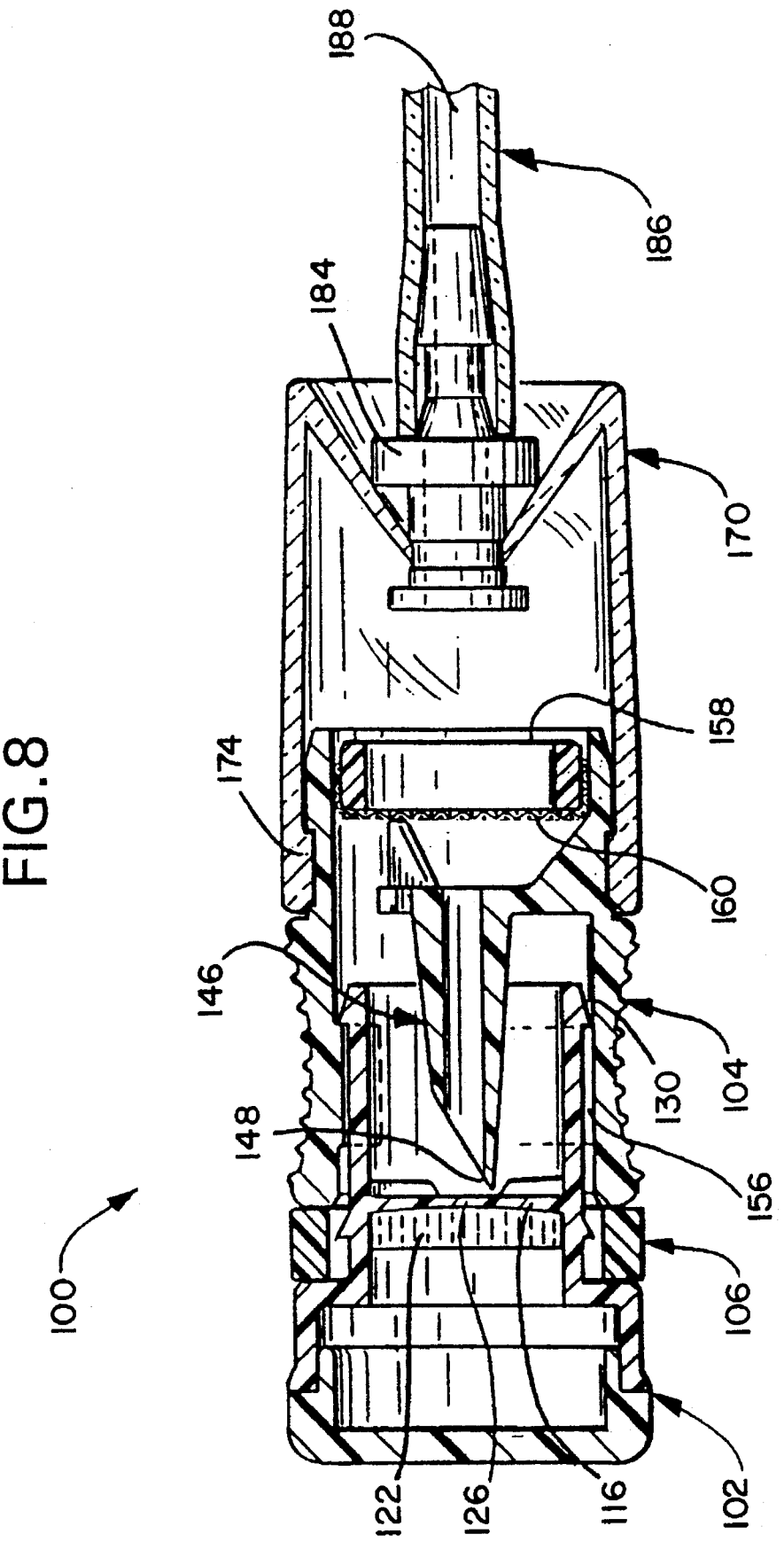
FIG. 8 is a plan view in section of the assembled device of FIG. 5, prior to use.

FIG. 8 illustrates the assembled device 100 prior to use, with an adapter 170 affixed thereto. The adapter 170 comprises a cylindrical tubular body 172 formed of a soft thermoplastic elastomer, such as Schafer, GmbH THEKA-FLEX, S 2030 M. A shallow inwardly facing annular flange 174 at a proximal end 176 of the adapter body 172 is received within a correspondingly shallow annular groove about the opener body 140 to hold the adapter 170 to the device 100.

A truncated cone 178 extends inwardly, proximally, from a distal end 180 of the adapter body 172 and terminates in a central opening 182. A luer fitting 184 of an instrument to be sterilized 186 having a lumen 188 therein, is shown received within the opening 182. Those of skill in the art will appreciate that the dimensions of the cone 178 can be varied to accommodate various types of instruments to be sterilized and that other engaging means may be substituted therefor.

Figure 9:
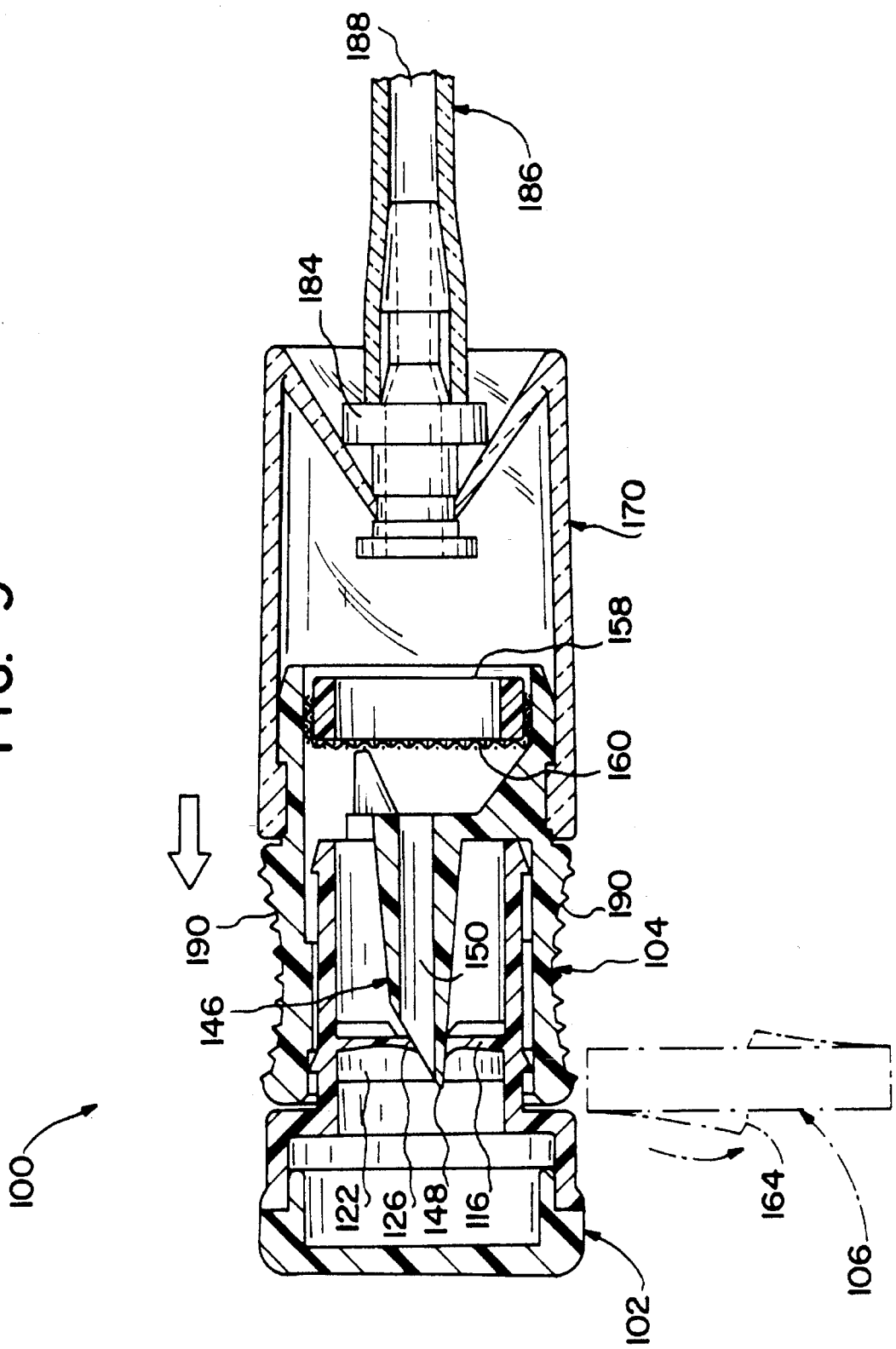
FIG. 9 is a plan view in section of the assembled device of FIG. 5, during use.
Figure 10:
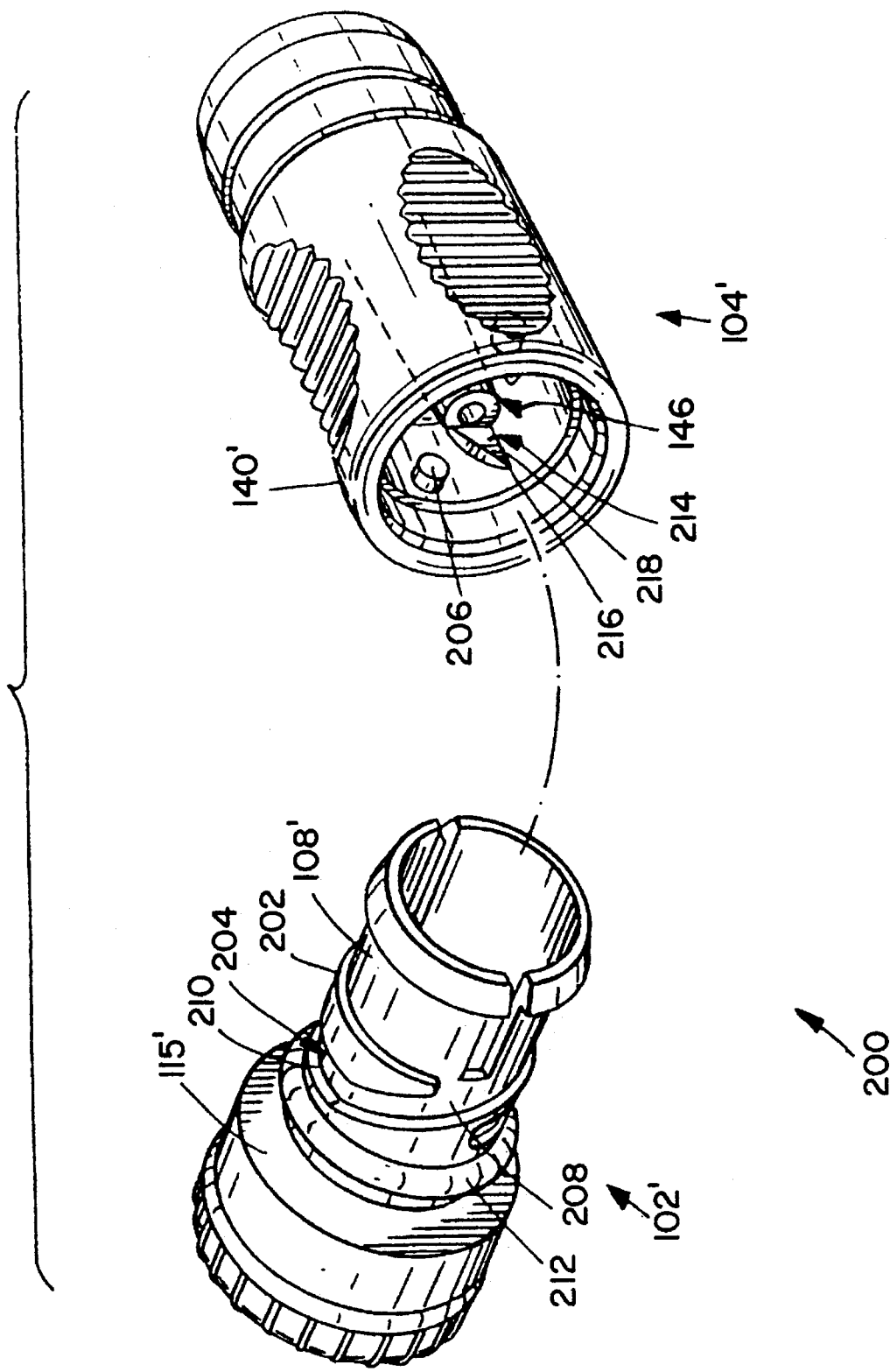
FIG. 10 is a perspective disassembly view of a further embodiment of a device of the present invention.
Figure 11:
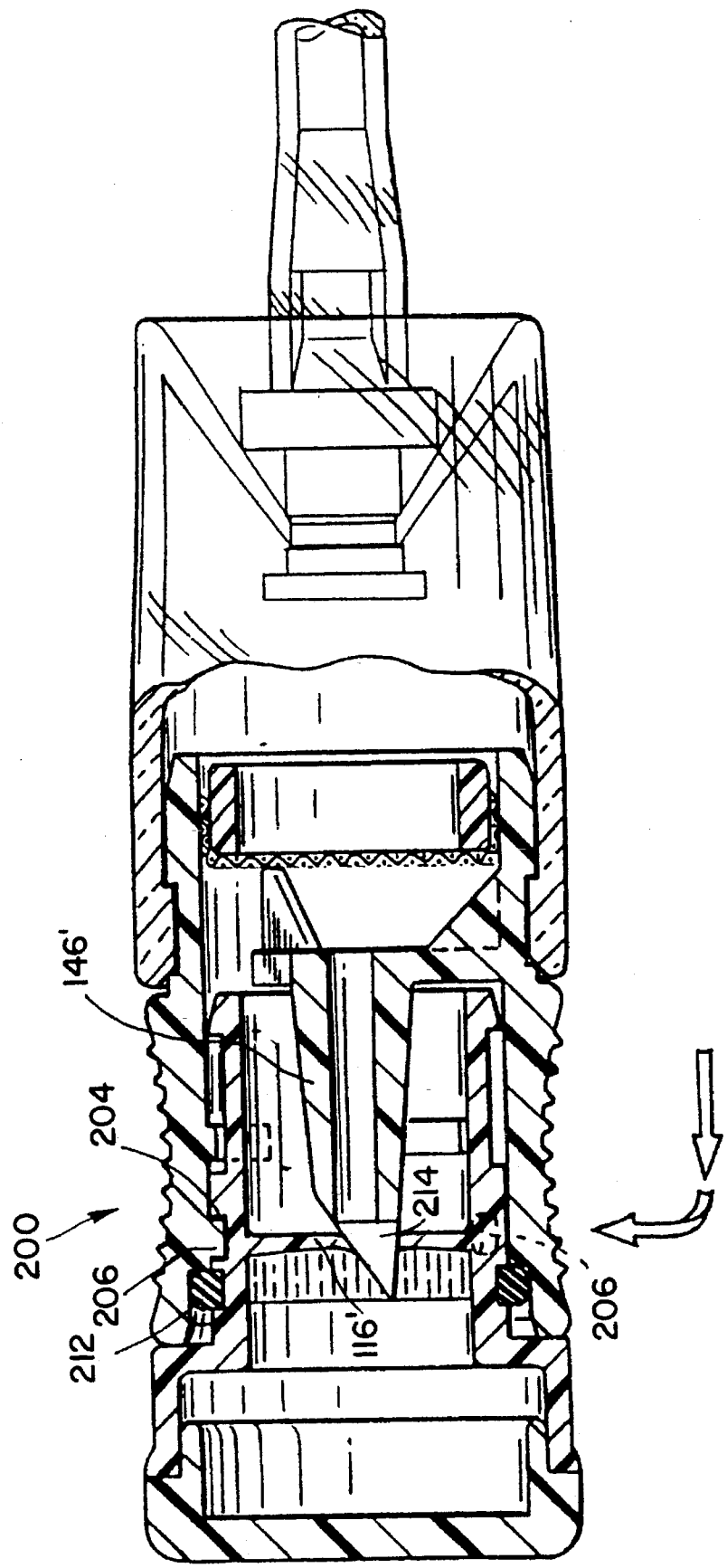
FIG. 11 is a plan view in section of the assembled device of FIG. 10, during use.

To use the device 100, an appropriately sized adapter 170 is selected for the particular instrument 186 to be sterilized. The adapter 170 is attached to the device 100 as shown in FIG. 8. The pull-tab 166 on the safety ring 106 is grasped and pulled to separate the safety ring thin wall section 164 and remove the safety ring 106 from the device 100. To aid the user in removing the safety ring 106 and in later rotating the capsule 102 relative to the opener 104, the opener body 140 is provided with several textured finger indentations 190 for easier grasping. After the safety ring 106 is removed, the capsule 102 and opener 104 are pushed together so that the spike 146 breaches the membrane wall 116 as shown in FIG. 9. Preferably, the capsule 102 is then rotated one full turn to ensure proper breaching of the membrane wall 116. The antimicrobial 122 is then free to leave the chamber 124 and flow into the instrument lumen 188.

In general practice, the device 100, with adapter 172 and instrument 186 attached as the membrane wall breached 116 as shown in FIG. 9 are then placed into the sterilization chamber (not shown ) of a solution vapor sterilizer (also not shown). A vacuum applied to the sterilization chamber causes the antimicrobial 122 to vaporize and migrate into the instrument lumen 188 to effect sterilization thereof.

FIGS. 10 to 13 illustrate a further embodiment of a device 200 according to the invention. The device 200 is similar in nearly all respects to the device 100 with the exception of the following differences. Accordingly, portions of the device 200 which are identical to the device 100 and were previously described with respect thereto, will be designated with like referenced numerals having a prime symbol (').

To reduce the force a user must exert to breach the membrane wall 116' the capsule 102' threads into the opener 104'. A raised embossment 202 surrounds the capsule body 108' adjacent the lip 115'. A pair of threads 204 formed in the embossment 202 receive, respectfully, a pair of pins 206 which project into the opener body 140'. Each thread 204 comprises a camming portion 208 and a circumferential portion 210.

The pins 206 enter the threads 204 through the camming portions 208 as the capsule 102' is rotated relative to the opener 104', thereby pulling the capsule 102' axially into the opener 104'. The circumferential portion 210 of the threads 204 allows the capsule 102' to be rotated an additional one quarter turn after it is fully received within the opener 104' to insure proper breaching of the membrane wall 116'.

In the previous embodiment, the interaction of the central flange 134 and the opener body 140 seals the capsule 102 to the opener 104 to prevent antimicrobial 122 from leaking out of the device 100 between the capsule 102 and opener 104. In the present embodiment, an O-ring 212 about the capsule body 108' replaces the central flange 136 and engages the opener body 140' to seal the capsule 102' therein.

In the previous embodiment, the spike 146 is provided with a simple bevelled tip 148 to penetrate the membrane wall 116. In the present embodiment, the bevelled tip 148 is replaced by a cutting tip 214 which is placed off of the central axles of the spike 146' and which acts in a fashion similar to that of a can opener to cut open the membrane wall 116. It will be understood that the cutting tip 214 may take various forms, however a sharp apex 216 and a sharp leading cutting edge 218 improve its cutting ability.

Proper breaching of the membrane wall 116' is a prerequisite to adequate sterilization. Accordingly, operators of the devices 100 or 200 prefer some tactile, audible, visual or other feedback that the device has been operated properly. In the previous embodiment, breaching of the membrane wall 116 tends to occur suddenly, thus driving the capsule 102 and opener 104 together in a violent manner creating both an audible and tactile snap. Also, the lip 115 will abut or closely approach the capsule body proximal end 142 in this position to provide a visual indication of proper operation.

In the present embodiment, the threading interaction between the capsule 102' and opener 104' breaches the membrane wall 116' more gently than in the previous embodiment. Thus, the user receives less tactile feedback that the membrane wall 116' has been breached. It may be desirable to provide such feedback in the form of a snapping interaction between parts on the capsule 102' and opener 104' or perhaps to provide a visual indication or other feedback that the opener 104' is fully actuated.

Figure 12:
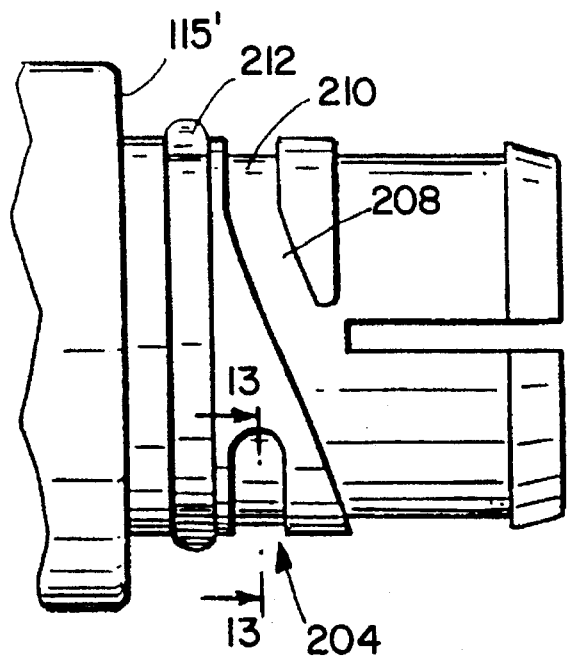
FIG. 12 is a close-up plan view of a distal portion of a capsule portion of the device of FIG. 10.
Figure 13:
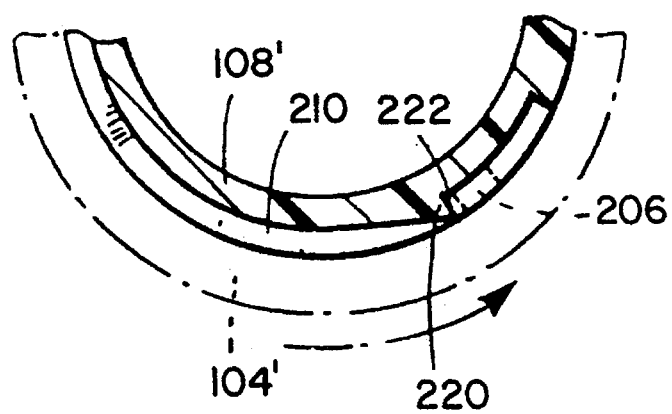
FIG. 13 is a sectional view taken along lines 13–13 of FIG. 12.

FIGS. 12 and 13 illustrate one method of providing such feedback. As each pins 206 travels its respective thread circumferential portion 210, it encounters a detent 220. The pins 206 cam over the detents 220 and snap over a sharp trailing edge 222 thereon to become trapped beyond the detents 220. Thus, the detents 220 provide both an audible and tactile feedback that the proper interaction has been achieved between the capsule 102' and opener 104'. Further, they prevent the capsule 102' and opener 104', and further prevent the capsule 102' from being easily backed out of the opener 104'. Alignment marks (not shown) or other visual indicia mark also be provided on the capsule 102' and opener 104' to indicate full actuation.

Although the present invention has been described in terms of specific devices for use in a preferred method of vapor sterilization, it will be understood that various modifications in the device and method will be apparent to those skilled in the art and are within the scope of this invention.

What is claimed is:

1. A device for delivering an antimicrobial vapor to a lumen of an article during solution vapor sterilization, the device comprising:

a first member comprising a vessel having an inner sealed chamber containing an antimicrobial solution and a wall forming at least a portion of the chamber;

a connector in communication with the wall for connecting the vessel to the article lumen;

a second member connected to the first member in moveable relation thereto, the second member comprising an opening member whereby movement of the second member in a predetermined direction relative to the first member moves the opening member toward wall to open the wall and place the chamber into fluid communication with the article lumen;

wherein the chamber containing the antimicrobial solution may be opened and placed into communication with the article lumen with the connector connected to the article lumen whereby a user is thereby isolated from the antimicrobial solution during a process of opening the chamber.

2. A device according to claim 1 and further comprising a first abutting surface on the first member, a second abutting surface on the second member and a removable guard between the first and second abutting surfaces wherein the removable guard prevents the first and second members from moving together sufficiently to breach the wall.

3. A device according to claim 2 wherein the guard further comprises a contrasting appearance to the first and second members whereby the presence or absence of the guard can easily be visually determined.

4. A device according to claim 2 wherein the guard comprises a ring encircling the device between the first and second members.

5. A device according to claim 4 wherein the ring is inelastic whereby to remove the ring from between the first and second abutting surfaces it must be deformed beyond its elastic limit.

6. A device according to claim 1 wherein the opening member comprises a penetrating member for penetrating the wall.

7. A device according to claim 6 wherein the penetrating member comprises a spike having a first end which faces the wall and comprises a sharpened tip.

8. A device according to claim 7 wherein the spike further comprises a second end and a central lumen extending coaxially therethrough, the spike lumen having a first end at the first end of the spike and a second end, the second end of the spike lumen being in fluid communication with the connector whereby the vessel is placed into fluid communication with the article lumen through the spike lumen when the spike penetrates the wall.

9. A device according to claim 8 and further comprising a passage for the antimicrobial solution from the chamber to the connector exterior of spike lumen.

10. A device according to claim 9 wherein the second member is tubular and has an inner wall, the first and second members are disposed in telescoping relation to one another and the spike is supported within the second member by at least one post extending from the second member inner wall wherein the spike is spaced therefrom to form the passage exterior of the spike lumen.

11. A device according to claim 1 wherein the first and second members are interconnected in telescoping relationship with each other.

12. A device according to claim 11 and further comprising a first detent extending from one of the first and second members and a first surface extending from the other of the first and second members, the first detent engaging the first surface to limit the degree to which the first and second members can telescope apart, wherein the other of the first and second members is free from obstructions such that the first and second members can move from a position with the first detent and first surface engaged to a position wherein the opening member contacts the wall without interference with each other.

13. A device according to claim 11 wherein one of the first and second members comprises a projection and the other of the first and second members is tubular and telescopically receive the projection therein.

14. A device according to claim 11 wherein the second member is tubular and wherein a projection on the first member extends axially from adjacent the wall and is telescopically received within the second member.

15. A device according to claim 14 wherein the connector is disposed at the proximal end of the second member whereby the vessel can be placed into fluid communication with the article lumen through the tubular second member and through the connector.

16. A device according to claim 14 and further comprising a mist filter in the second member between the first member and the connector to prevent liquid antimicrobial solution or contaminants from entering the article lumen.

17. A device according to claim 14 wherein the opening member comprises a spike received within the second member in a position to breach the wall when the first and second members are telescoped together.

18. A device according to claim 17 wherein the spike further comprises a first end facing the wall, a second end and a central lumen extending coaxially therethrough, the spike lumen having a first end at the first end of the spike and a second end, the second end of the spike lumen being in fluid communication with the connector whereby the vessel is placed into fluid communication with the article lumen through the spike lumen when the spike penetrates the wall.

19. A device according to claim 18 and further comprising a first abutting surface on the first member, a second abutting surface on the second member and a removable guard between the first and second abutting surfaces wherein the removable guard prevents the first and second members from moving together sufficiently to breach the wall.

20. A device according to claim 14 and further comprising a threaded interconnection between the first and second members wherein rotation of the first and second members relative to each other moves them together to breach the wall.

21. A device according to claim 20 wherein the device further comprises a sharp leading cutting edge on the spike which is positioned so that when the first and second members are rotated together, the cutting edge cuts through the wall.

22. A device according to claim 20 and further comprising a tactile detent on one of the first and second members positioned to engage a tactile detent engaging surface on the other of the first and second members as the first and second members are rotated together whereby the interaction of the tactile detent and the tactile detent engaging surface produces a tactile feedback to a user that the first and second members are fully rotated together.

23. A device according to claim 20 wherein the projection comprises a thread, the second member comprises a thread engaging protuberance and wherein the tactile detent is disposed within the thread and wherein the tactile detent engaging surface comprises the thread engaging protuberance.

* * * * *